US008827908B2

(12) United States Patent
Pellegretti

(10) Patent No.: US 8,827,908 B2
(45) Date of Patent: Sep. 9, 2014

(54) APPARATUS FOR ULTRASOUND IMAGING

(75) Inventor: Paolo Pellegretti, Genova (IT)

(73) Assignee: Esaote S.p.A., Genoa (IT)

( * ) Notice: Subject to any disclaimer, the term of this patent is extended or adjusted under 35 U.S.C. 154(b) by 0 days.

(21) Appl. No.: 13/539,061

(22) Filed: Jun. 29, 2012

(65) Prior Publication Data

US 2013/0006114 A1   Jan. 3, 2013

(30) Foreign Application Priority Data

Jun. 30, 2011   (IT) .............................. GE2011A0067

(51) Int. Cl.
*A61B 8/00* (2006.01)
*G01N 29/04* (2006.01)
*A61B 8/08* (2006.01)
*A61B 8/14* (2006.01)
*A61B 8/15* (2006.01)

(52) U.S. Cl.
CPC ................. *A61B 8/406* (2013.01); *A61B 8/403* (2013.01); *A61B 8/0825* (2013.01); *A61B 8/14* (2013.01); *A61B 8/15* (2013.01); *A61B 8/4281* (2013.01); *A61B 8/463* (2013.01); *Y10S 128/915* (2013.01)
USPC .............. 600/447; 600/443; 73/624; 128/915

(58) Field of Classification Search
USPC ............ 600/407, 443, 447, 448; 73/612, 620, 73/621, 624; 128/915
See application file for complete search history.

(56) References Cited

U.S. PATENT DOCUMENTS

| 4,478,084 A | 10/1984 | Hassler |
| 4,509,368 A | 4/1985 | Whiting |
| 4,541,436 A | 9/1985 | Hassler |
| 5,115,805 A * | 5/1992 | Bommannan et al. ............ 601/2 |
| 6,254,614 B1 * | 7/2001 | Jesseph ......................... 606/130 |
| 8,376,947 B2 * | 2/2013 | Rambod et al. ............... 600/437 |
| 2005/0143638 A1 | 6/2005 | Johnson |

OTHER PUBLICATIONS

Italian Misnitry of Economic Development, Search Report, Dec. 16, 2011.

* cited by examiner

*Primary Examiner* — Michael Rozanski
(74) *Attorney, Agent, or Firm* — Themis Law

(57) ABSTRACT

An apparatus for ultrasound imaging of a body, particularly a breast of a patient, includes ultrasonic pulse-emitting and pulse-receiving units, disposed in facing relationship at a predetermined distance from each other on opposite sides of a compartment for receiving the body, ultrasonic pulses emitted by the emitting unit and received by the receiving unit after passing through the body being converted into transmit signals; and an ultrasonic pulse emitting and receiving unit disposed to define a scan plane substantially perpendicular to the coronal plane of the patient and having one or more electro-acoustic transducers, which emit ultrasonic pulses into the body and receive echoes generated by the anatomic structures of the body, the echoes being converted into reflection signals. An acoustic impedance adaptation medium, particularly a liquid, preferably water, is interposed between the emitting unit and/or the receiving unit and/or the emitting and receiving unit and the breast.

20 Claims, 9 Drawing Sheets

APPARATUS FOR ULTRASOUND IMAGING

FIELD OF THE INVENTION

The present invention relates to an apparatus for ultrasound imaging of a body under examination, particularly a breast of a patient. More particularly, the invention relates to an apparatus which includes, in one embodiment:

an ultrasonic pulse-emitting unit having one or more electro-acoustic transducers and an ultrasonic pulse-receiving unit having one or more electro-acoustic transducers, the emitting unit and the receiving unit being in mutually facing relation and at a predetermined distance from each other, thereby being located on opposite sides of a compartment for receiving the breast, the ultrasonic pulses emitted by the emitting unit being received by the receiving unit after passing through the body under examination and being converted into transmit signals;

an ultrasonic pulse emitting and receiving unit having one or more electro-acoustic transducers for emitting ultrasonic pulses into the breast and for receiving echoes generated by the anatomic structures of the breast, which echoes are converted into reflection signals; and a control unit for controlling the emitting unit and the emitting and receiving unit, a processing unit for processing the received signals, and units generating and displaying the images, wherein an acoustic impedance adaptation medium, particularly a liquid, most preferably water, is interposed between the emitting unit and/or the receiving unit and/or the emitting and receiving unit and the breast.

BACKGROUND OF THE INVENTION

Apparatus for ultrasound imaging are known and widely used, mainly for 3D breast scanning 3D ultrasound imaging of a breast placed in a liquid bath, preferably in water, has certain advantageous characteristics, for example, distortions in structure detection may be prevented, and the process is inherently safer.

Nevertheless, the pulses emitted by the emitting unit or the emitting and receiving unit are required to pass through at least two interfaces made of materials having different acoustic impedances.

Particularly, when water is the acoustic impedance adaptation medium, a water-skin interface is added, which has a high acoustic impedance mismatch.

A number of undesired effects occur at this interface, including high reflection, which involves lower energy transmission, and high refraction, which involves divergence of the acoustic beams from the ideal straight path.

These effects, which can be found in prior art apparatus, lead to a decrease of sensitivity, and affect spatial resolution of images.

In prior art apparatus, this problem is yet unsolved and the need still exists for technical solutions that might limit reflection and refraction.

These apparatus also showed a new scanning problem, which was not found in standard handheld ultrasound probes.

If the transmitted pulses have an angle of incidence of more than 60°, the signal intensity is attenuated.

The worst condition occurs when the angle of incidence is close to a critical angle of about 66°, which somewhat creates a threshold effect.

A prior art apparatus is disclosed, for instance, in U.S. Pat. No. 7,771,360, incorporated herein by reference, in which the emitting and receiving unit performs scans on planes that are substantially parallel to the coronal plane of the patient.

This leads to a general degradation of image quality in the areas in which the angles of incidence fall close to the above values, and particularly in the area of the nipple, the trunk wall, or in case of a small breast.

SUMMARY OF THE INVENTION

The present invention has the object of obviating the above drawbacks of prior art apparatus by an apparatus as described hereinafter. An apparatus according to the invention has a shape changing element for changing the shape of the breast, so that, for most of the surface of the breast, the lines of view of the ultrasonic pulses emitted by the emitting and receiving unit are incident on the surface at an angle of less than 70°, preferably less than 66°, to the normal of the plane tangent to the surface of the breast at the point of incidence.

Thus, breast positioning is restricted, to limit the reflection and refraction effects that start to occur with angles of incidence of more than 60° and are particularly evident with angles of incidence of more than 66° to the normal of the plane tangent to the breast surface in the incidence point, thereby improving penetration of ultrasonic pulses and hence image quality.

As an additional advantage, patient positioning is simplified.

In a first embodiment, the shape changing element is a breast retaining or modeling ring, which is placed around the breast.

The ring is made of an acoustically "transparent" material, which will cause no significant reflection, which might lead to a loss in the transmitted signal, and will also adapt to the impedance of the media between which it is interposed (water/water+PEG and skin) to ensure a lower refraction, with the same incidence angle.

Materials with such characteristics, which might be used to form the ring belong, for instance, to the group comprising silicones, polyurethanes, urethanes and agaroses.

The breast retaining and modeling ring is particularly advantageous in the breast area close to the patient's trunk because, when the retaining ring is in this area, the breast surface may be modeled into a predetermined shape, thereby avoiding the above mentioned angles of incidence.

Therefore, the shape changing element allows the breast portion proximal to the rib cage to be remodeled to ensure that the angles of incidence of ultrasounds are as far as possible from the critical angle.

In a further embodiment, size adjustment means are provided for adjusting the size of the shape changing element, to allow the shape changing element to fit various breast sizes, changing from patient to patient, thereby optimizing the shape modeling function while providing high comfort to the patient.

In an alternative embodiment, the shape changing element is a retaining cup placed around the breast.

Thus, the entire breast is contained in such retaining cup, whose shape may be designed to avoid the above mentioned angles of incidence.

According to a further improvement, the shape changing element is made of a material having an acoustic wave propagation velocity and a density substantially equal to those of water.

This will counterbalance the disadvantageous addition of interfaces caused by the use of the shape changing element, through which the ultrasonic pulses are designed to pass.

The present invention further relates to an apparatus as described hereinbefore, in which the emitting and receiving unit is arranged to define a scan plane substantially perpendicular to the coronal plane of the patient.

The scan plane may be any plane, including a plane parallel to or coincident with the sagittal plane or the axial plane.

Due to the conformation of the breast, an emitting and receiving unit oriented to define a scan plane substantially perpendicular to the coronal plane of the patient will avoid angles of incidence equal to or larger than the above mentioned threshold values, and will advantageously limit reflection and reflection, thereby improving image quality.

This is particularly advantageous when scanning a small breast, with remarkable improvements in image quality therefor.

As compared with prior art apparatus, an emitting and receiving unit arranged to define a scan plane substantially perpendicular to the coronal plane of the patient will improve the spatial resolution in the direction perpendicular to the coronal plane, which is affected, in prior art apparatus, by a different degree of the focusing force in the scan plane parallel to the coronal plane and in the direction perpendicular to the coronal plane.

This is directly caused by the impossibility of achieving accurate electronic focusing in the direction perpendicular to the coronal plane.

However, the apparatus of the present invention advantageously provides a spatial resolution in the plane perpendicular to the coronal plane that is comparable to that of the coronal plane itself, thereby affording even spatial resolutions in the three spatial dimensions, and achieving voxel isotropy.

In a further exemplary embodiment, the unit for processing the received signals generates a propagation velocity map from the transmit signals.

Therefore, the images are generated on the basis of the reflection signals and are recorded according to the propagation velocity map.

The synergistic effect of information retrieved from the transmit signals received by the receiving unit and from the reflection signals received by the emitting and receiving unit advantageously provides improved quality images and allows correction according to the propagation velocity measured at each point.

In a further embodiment, the ultrasonic pulses emitted by the emitting and receiving unit are focused to a depth corresponding to the dense tissue of the breast.

Concerning the dense tissue of the breast, internal heterogeneities act as impedance mismatch interfaces, which disturb the acoustic beams with path deviation or intensity attenuation effects.

Simulation of individual beams using actual imaging codes and use of real propagation velocity data clearly show the presence of these effects.

This causes an apparent focusing consistency loss, which results in a lower signal-to-noise ratio and blurred structure images.

Internal breast structures have a generally radial architecture, whereby acoustic beams impinge upon strongly irregular shapes when performing scans over a plane substantially parallel to the coronal plane of the patient, with considerably variable angles of incidence for the various acoustic beams.

However, when the scan plane is substantially perpendicular to the coronal plane, regular surfaces are found, with similar angles of incidence for the various acoustic beams, which will reduce the defocusing effect.

This will reduce focusing aberrations in dense breast tissue scanning, caused by the internal breast capsule physiology.

In a further embodiment, a second ultrasonic pulse emitting and receiving unit is provided, which includes one or more electro-acoustic transducers for emitting ultrasonic pulses into the breast and receiving the echoes generated by the anatomical structures of the breast, which echoes are converted into reflection signals, which second emitting and receiving unit is arranged to define a scan plane substantially parallel to the coronal plane of the patient.

The images generated by the second emitting and receiving unit are combined with the images generated by the emitting and receiving unit.

Thus, the reflection signals of the emitting and receiving unit integrate the information retrieved from the reflection signals of the second emitting and receiving unit.

In a further exemplary embodiment, the lines of view of the ultrasonic pulses emitted by the emitting and receiving unit are oriented towards the rib cage of the patient by steering.

This feature improves scanning of the area proximal to the rib cage because electronic steering affords better angles of incidence of ultrasounds against the breast surface, as compared with those obtained, in similar conditions, by scanning on planes parallel to the coronal plane.

According to an alternative exemplary embodiment, the lines of view of the ultrasonic pulses emitted by the emitting and receiving unit are oriented towards the rib cage of the patient by manual or automatic orientation of the emitting and receiving unit.

This will further avoid angles of incidence with values similar to the above mentioned critical values.

In yet another exemplary embodiment, the emitting and receiving unit is arranged to define a scan plane substantially parallel to the coronal plane of the patient, the scan plane being further oriented towards the rib cage of the patient by steering.

A further configuration may be envisaged, in which the emitting and receiving unit is arranged to define a scan plane substantially perpendicular to the coronal plane of the patient, the second emitting and receiving unit being arranged in combination to define a scan plane substantially parallel to the coronal plane of the patient, and the scan plane of such second emitting and receiving unit being oriented towards the rib cage of the patient by steering.

In a preferred embodiment, the lines of view of the ultrasonic pulses emitted by the emitting and receiving unit are incident on the surface of the breast at an angle less than 70°, preferably less than 66°, to the normal of the plane tangent to the surface of the breast in the incidence point.

Even better results in terms of image quality may be achieved by maintaining the angle of incidence below 60°.

The present invention also relates to an apparatus as described hereinbefore, in which the water is added with polyethylene glycol (PEG).

The presence of PEG in solution has a remarkable effect on the propagation velocity of ultrasonic pulses, as confirmed by acoustic test measurements.

This will reduce acoustic velocity mismatch with patient's breast tissues.

Therefore, the addition of PEG to the solution affords propagation velocity adjustment, by changing the amount of added PEG.

The addition of PEG also imparts degassing properties to the solution, i.e. removes the small suspended gas bubbles from the liquid and reduces the level of dissolved gas below the natural equilibrium level.

In a preferred exemplary embodiment, the polyethylene glycol is added in an amount from 1% to 40%, preferably from 10% to 30%, particularly 20%.

Experimental studies showed that, even with angles of incidence of transmit pulses exceeding 60° and particularly 66°, the addition of 20% PEG eliminates the signal intensity attenuation effects, which occur with PEG-free water, as mentioned above.

The combination of the above features and their combined use affords a consistent optimization of 3D breast scanning using integrated transmission and reflection ultrasound techniques.

BRIEF DESCRIPTION OF THE DRAWINGS

These and other features and advantages of the present invention will appear more clearly from the following description of a few embodiments, illustrated in the annexed drawings, in which.

DETAILED DESCRIPTION OF EMBODIMENTS OF THE INVENTION

Figure 1:
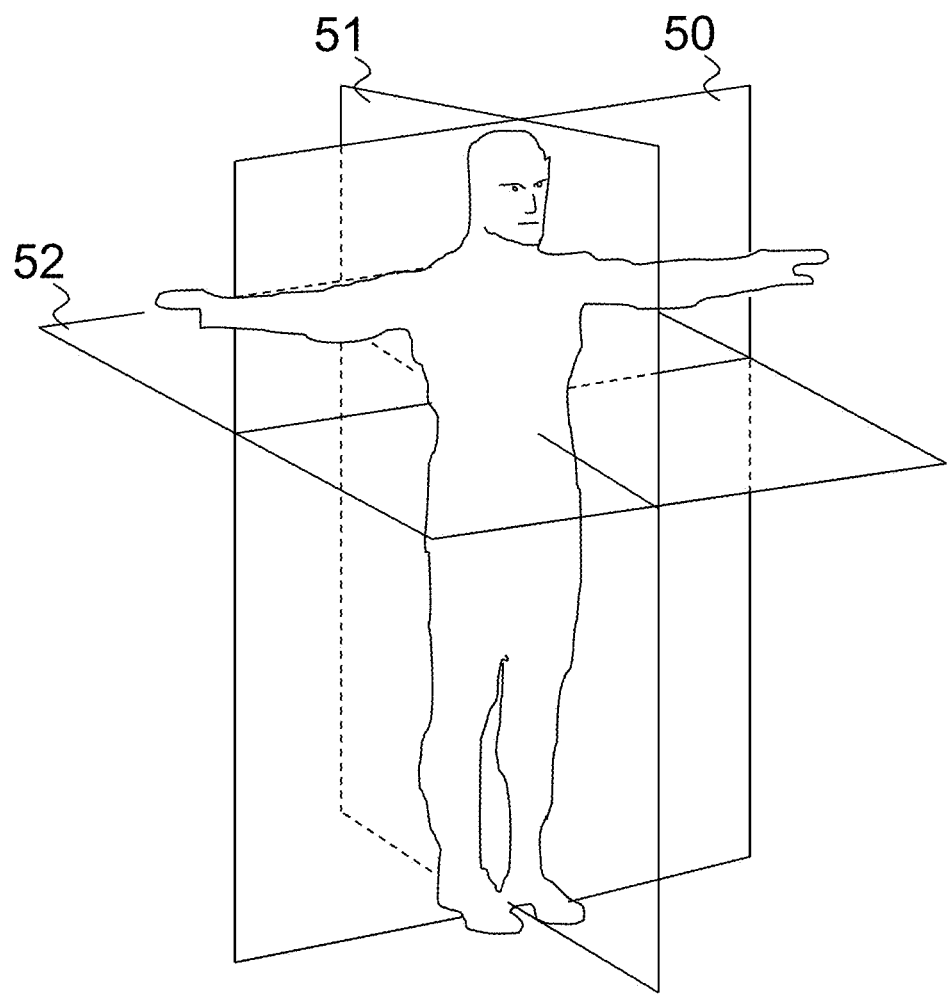
FIG. 1 defines the planes of the human body according to standard nomenclature.

FIG. 1 defines the anatomical planes of the human body according to the standard nomenclature: the coronal plane 50 that divides the body into dorsal and ventral or back and front parts, the sagittal plane 51 that divides the body into right and left parts and the axial plane 52 that divides the body into cranial and caudal parts.

Figure 2:
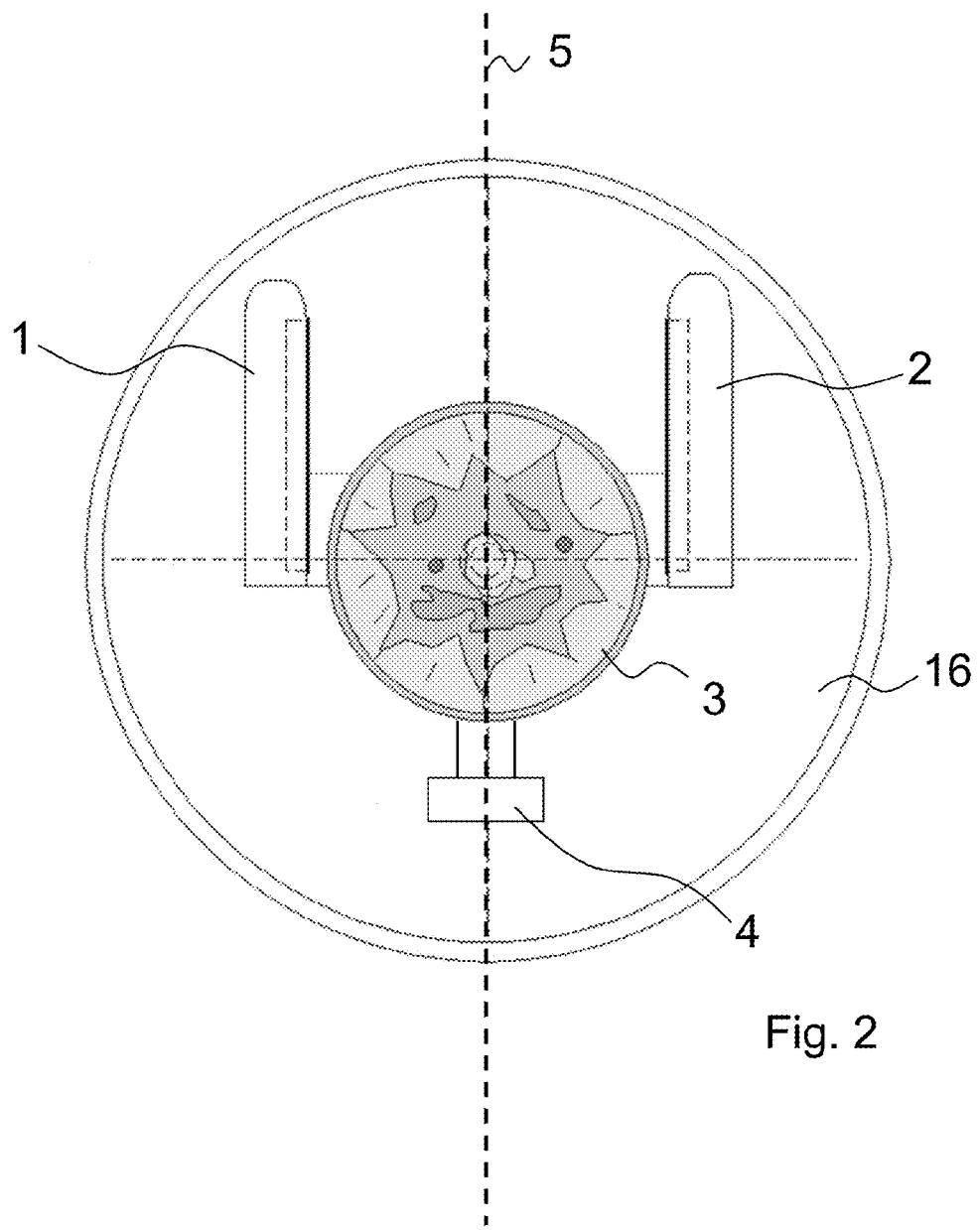
FIG. 2 is a top view of an apparatus according to the invention.
Figure 3:
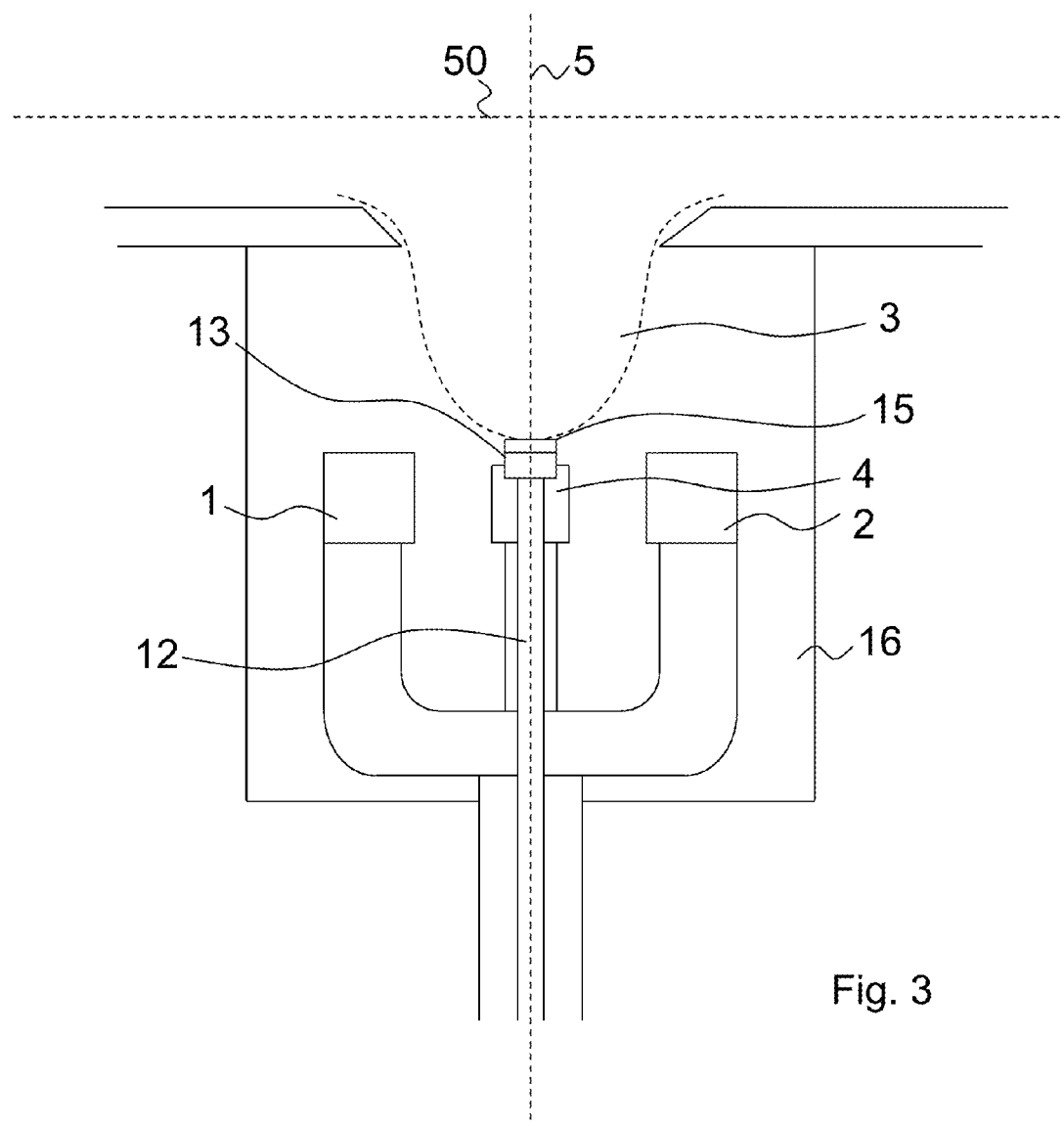
FIG. 3 is a side view of an apparatus according to the invention.

FIGS. 2 and 3 show different views of the apparatus for ultrasound imaging of a body under examination according to the present invention. By "body" it is intended an entire body of a patient or a part thereof, for example, a breast 3.

The apparatus includes an ultrasonic pulse emitting unit 1 having one or more electro-acoustic transducers and an ultrasonic pulse receiving unit 2 having one or more electro-acoustic pulses.

The emitting unit 1 and the receiving unit 2 are in mutually facing relation and at a predetermined distance from each other, thereby being located on opposite sides of a compartment for receiving the breast 3.

The ultrasonic pulses emitted by the emitting unit 1 are received by the receiving unit 2 after passing through the breast 3 and are converted into transmit signals.

An ultrasonic pulse emitting and receiving unit 4 is also provided, which includes one or more electro-acoustic transducers for emitting ultrasonic pulses into the breast 3 and for receiving echoes generated by the anatomic structures of the breast 3, which echoes are converted into reflection signals.

A control unit for controlling the emitting unit 1 and the emitting and receiving unit 4, a processing unit for processing the received signals, and units generating and displaying images, not shown, are also provided.

An acoustic impedance adaptation medium 16, particularly a liquid, preferably water, is interposed between the emitting unit 1 and/or the receiving unit 1 and/or the emitting and receiving unit 4 and the breast 3.

The breast is held in position by a rod 12 which cooperates with the breast 3 itself, e.g. via a pair of magnets 13 and 15, and the emitting unit 1, the receiving unit 2 and the emitting and receiving unit are respectively placed at the ends of a support element having three arms, which can translate and/or rotate about the breast 3.

The apparatus may be advantageously used for three-dimensional imaging.

The emitting and receiving unit 4 is arranged to define a scan plane 5 substantially perpendicular to the coronal plane 50.

The scan plane may be any plane, including a plane parallel to or coincident with the sagittal plane 51 or the axial plane 52.

The emitting and receiving unit 4 oriented to define a scan plane substantially perpendicular to the coronal plane 50 of the patient avoids angles of incidence equal to or larger than the threshold value of 66°, thereby limiting reflection and reflection at the interface.

Figure 4:
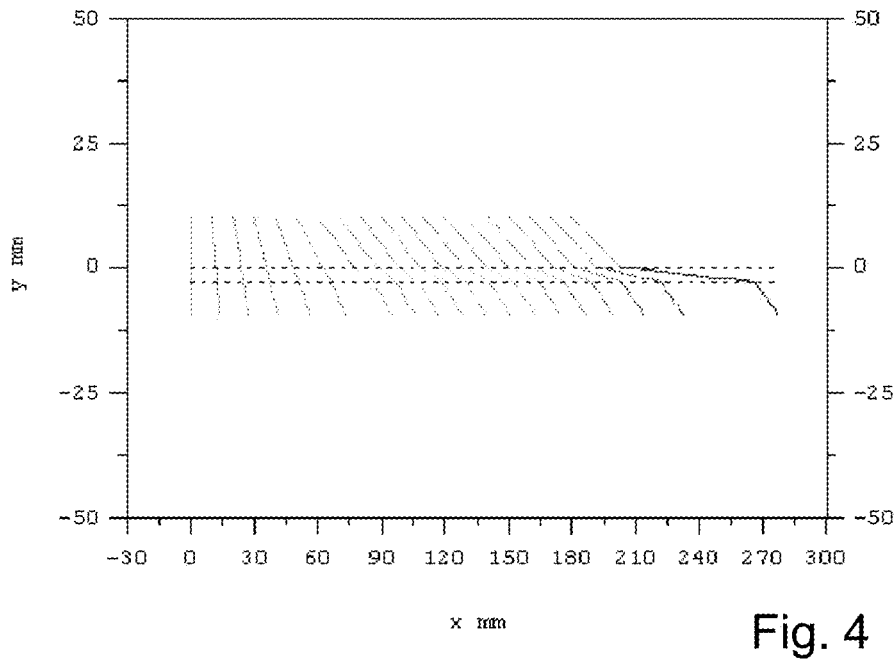
FIG. 4 shows a refraction model for a water-skin-fat interface for acoustic beams having different angles of incidence.

FIG. 4 shows a refraction model of a water-skin-fat interface, i.e. a double water-skin and skin-fat interface, with different refraction angles being shown for the acoustic beams that reach the interface at different angles of incidence.

As the angle of incidence increases, the angle of refraction also remarkably increases, especially in the thickness of the skin.

Figure 5:
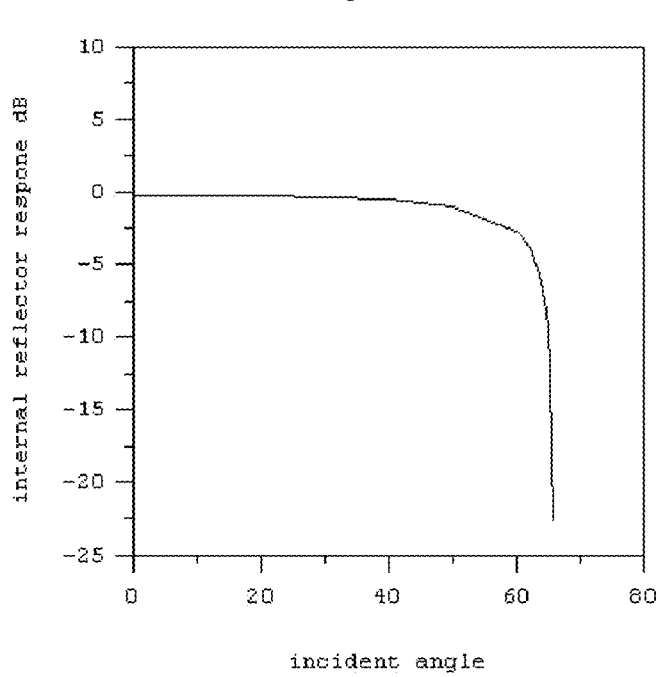
FIG. 5 shows signal attenuation in fat according to the angle of incidence.

The signal is strongly attenuated when the angle of incidence of the transmit pulses exceeds 60°, as shown in the diagram of FIG. 5, in which the signal intensity is displayed as a function of the angle of incidence.

It shall be noted that, for a critical value of about 66°, the signal amplitude is strongly reduced, which somewhat creates a threshold effect.

Figure 6:
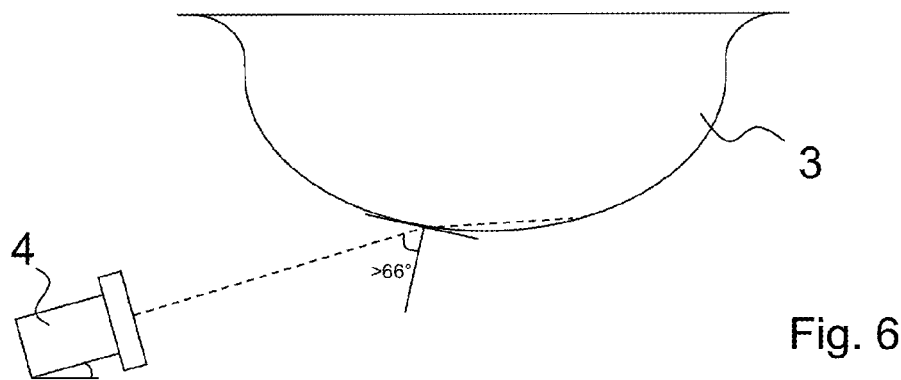
FIG. 6 shows an example, in which the acoustic beams reach the breast skin at an undesired angle of incidence.

This is also schematically shown in FIG. 6, in which the acoustic beams reach the breast at an angle of incidence of more than 66°, and are subjected to strong refraction.

In order to obviate this problem, the lines of view of the ultrasonic pulses emitted by the emitting and receiving unit 4 may be arranged to be oriented towards the rib cage of the patient.

Such orientation may be obtained by electronic steering, i.e. by pulse delay control by a beamformer, or by manual or automatic orientation of the emitting and receiving unit 4.

A second ultrasonic pulse emitting and receiving unit, not shown, may be also provided, which is arranged to define a scan plane substantially parallel to the coronal plane 50 of the patient.

The images generated by the second emitting and receiving unit may be combined with the images generated by the emitting and receiving unit 4.

In this case, steering may be performed on the acoustic beams of the emitting and receiving unit 4, of the second emitting and receiving unit, or both.

In an alternative exemplary embodiment, the emitting and receiving unit 4 is arranged to define a scan plane substantially parallel to the coronal plane 50 of the patient, which scan plane is further oriented towards the rib cage of the patient by steering.

Figure 7:
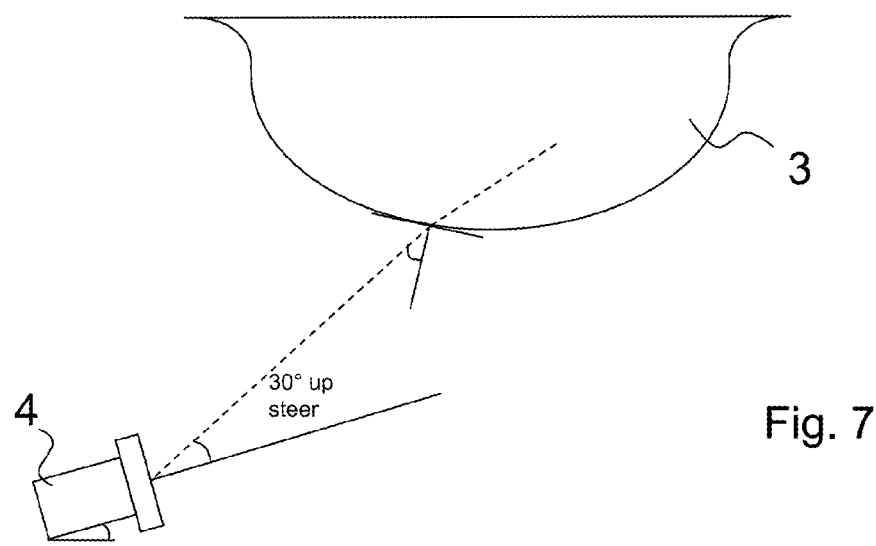
FIG. 7 shows an example, in which the angle of incidence is adjusted by steering acoustic beams.

In a preferred embodiment, shown in FIG. 7, the lines of view of the ultrasonic pulses emitted by the emitting and receiving unit are incident on the surface of the breast at an angle less than 70°, preferably less than 66°, to the normal of the plane tangent to the surface of the breast in the incidence point.

Figure 8:
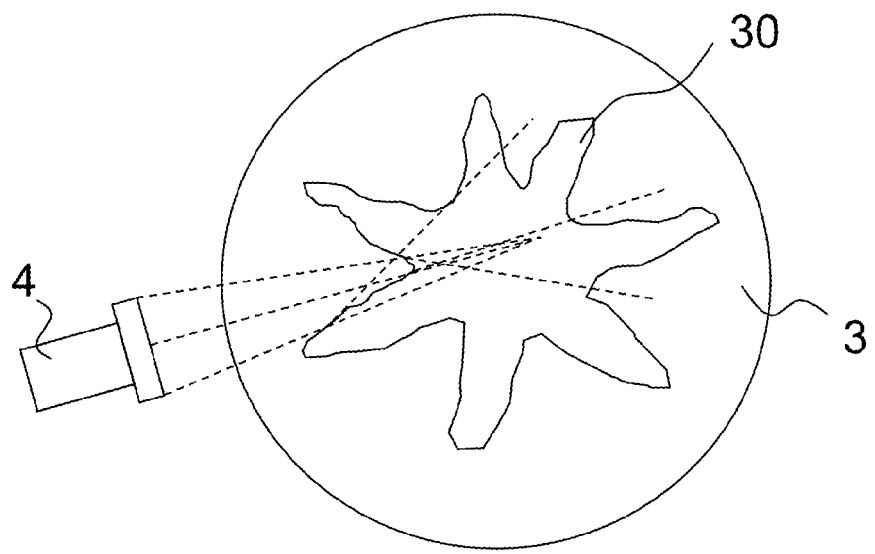
FIG. 8 shows a scan over a plane substantially parallel to the coronal plane, with focus on dense breast tissue.

FIG. 8 shows a scan over a plane substantially parallel to the coronal plane 50, in which the ultrasonic pulses emitted by the emitting and receiving unit 4 are focused to a depth corresponding to the dense tissue 30 of the breast 3.

As clearly shown, the internal heterogeneities of the dense tissue 30 act as impedance mismatch interfaces, which disturb the acoustic beams with path deviation or intensity attenuation effects.

The internal structures of the dense tissue 30 of the breast 3 have a generally radial architecture, whereby acoustic beams impinge upon strongly irregular shapes when performing scans over a plane substantially parallel to the coronal plane of the patient, with considerably variable angles of incidence for the various acoustic beams.

Figure 9:
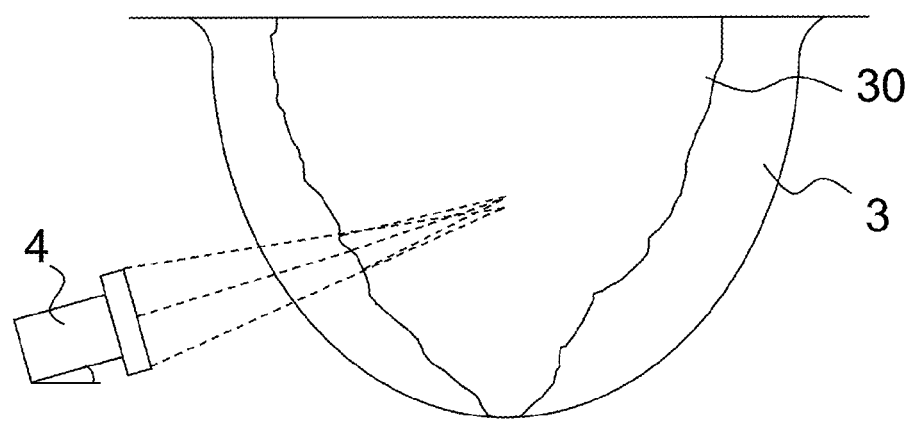
FIG. 9 shows a scan over a plane substantially perpendicular to the coronal plane, with focus on dense breast tissue.

However, when the scan plane is substantially perpendicular to the coronal plane 50, as shown in FIG. 9, more regular surfaces are found, with similar angles of incidence for the various acoustic beams, which will reduce the defocusing effect.

Figure 10:
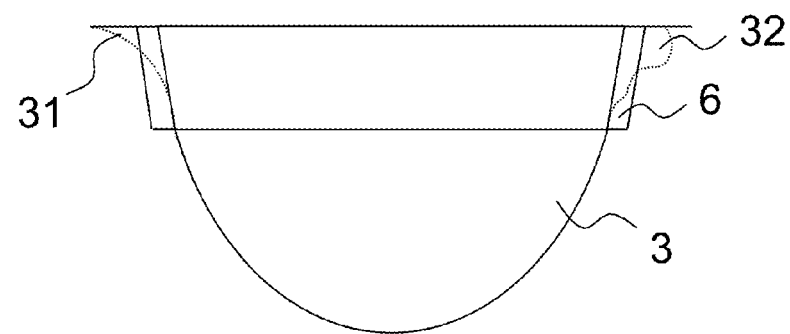
FIG. 10 shows an exemplary embodiment of a shape changing element in an apparatus according to the invention.

FIG. 10 shows a shape changing element 6 for changing the shape of the breast 3 so that, for most of the surface of the breast 3, the lines of view of the ultrasonic pulses emitted by the emitting and receiving unit are incident on the surface at an angle less than 70°, preferably less than 66°, to the normal of the plane tangent to the surface of the breast 3 in the incidence point.

In the illustrated exemplary embodiment, the shape changing element 6 is a retaining ring placed around the breast 3.

This is particularly advantageous in the breast area 3 close to the patient's trunk because, when the retaining ring is in this area, the breast surface may be modeled into a predetermined shape.

This will avoid the above mentioned angles of incidence, which would be found if the breast were free, as schematically shown by the broken line 31, or any irregular shapes, e.g. caused by skin pinching, as schematically shown by the broken line 32.

Size adjustment means may be further provided for adjusting the size of the shape changing element, to allow the shape changing element to fit various breast sizes, changing from patient to patient, thereby optimizing the shape modeling function while providing high comfort to the patient.

In an alternative embodiment, the shape changing element 6 is a retaining cup placed around the breast.

Figure 11:
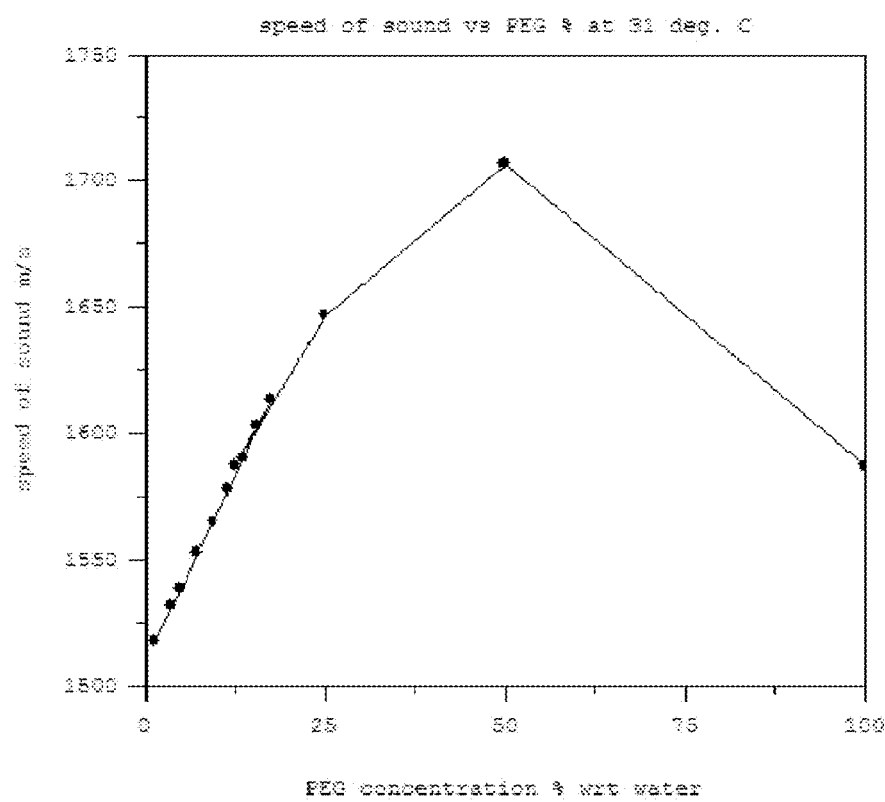
FIG. 11 shows a change of the propagation velocity of sound according to PEG concentration.
Figure 12:
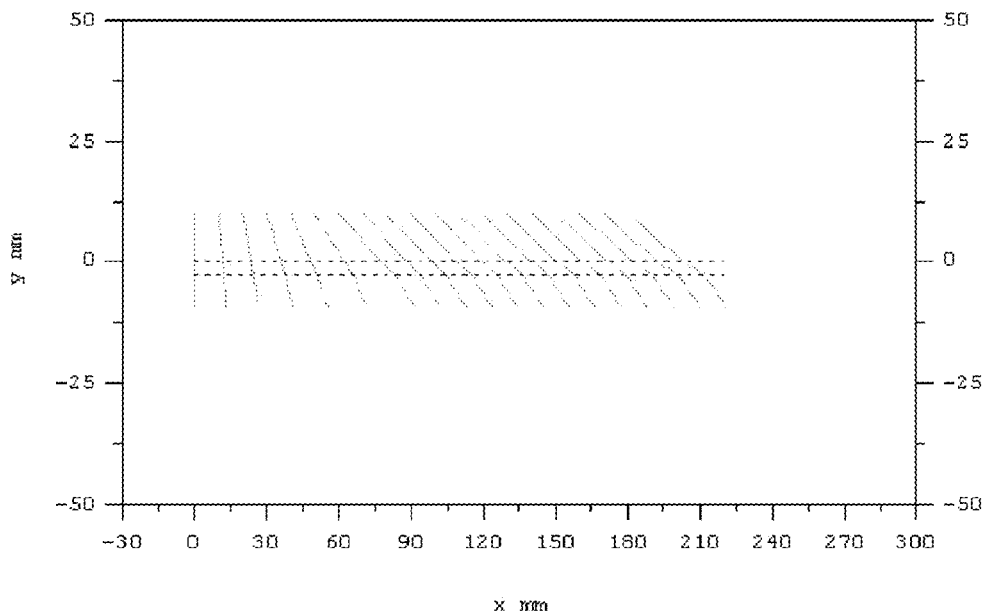
FIG. 12 shows a refraction model for a water/PEG-skin-fat interface for acoustic beams having different angles of incidence.
Figure 13:
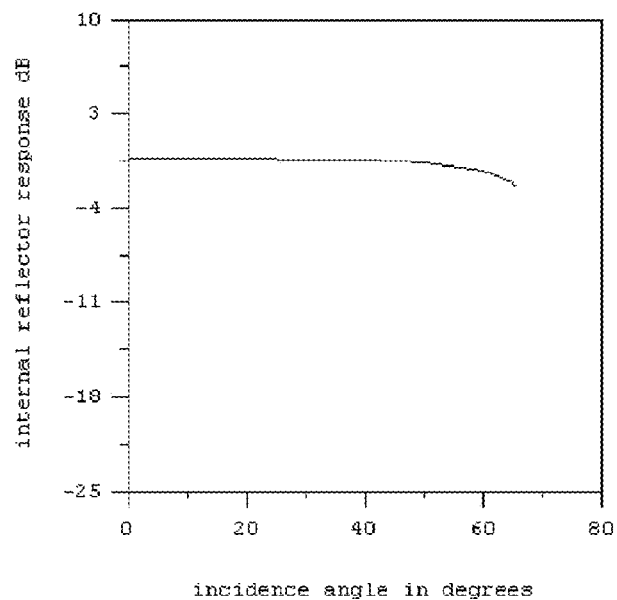
FIG. 13 shows signal attenuation in fat according to the angle of incidence, with a water and PEG solution.

FIGS. 11, 12 and 13 show charts concerning polyethylene glycol (PEG) addition to water 16.

The presence of PEG in solution has a remarkable effect on the propagation velocity of ultrasonic pulses, as confirmed by acoustic test measurements, as shown in FIG. 11.

Therefore, the addition of PEG to the solution affords propagation velocity adjustment, by changing the amount of added PEG.

Particularly, as PEG concentration increases, sound velocity initially increases in an almost linear fashion; then the curve ascends to a peak at 50% concentration, and decreases again.

The addition of PEG also imparts degassing properties to the solution, i.e. removes the small suspended gas bubbles from the liquid and reduces the level of dissolved gas below the natural equilibrium level.

In a preferred exemplary embodiment, the polyethylene glycol is added in an amount from 1% to 40%, preferably from 10% to 30%, particularly 20%.

Experimental studies showed that, even with angles of incidence of transmit pulses exceeding 60° and particularly 66°, the addition of 20% PEG eliminates the signal intensity attenuation effects, which occur with PEG-free water, as mentioned above.

FIG. 12 shows a refraction model of a water/PEG-skin-fat interface for acoustic beams having different angles of incidence, in which water has been added with 20% PEG; a comparison with the chart of FIG. 4 interestingly shows that refraction is strongly reduced.

FIG. 13 also clearly shows that, with 20% PEG, the threshold effect disappears.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become apparent to those skilled in the art and the scope of the present invention is limited only by the appended claims.

The invention claimed is:

1. An apparatus for ultrasound imaging of a body under examination, particularly a breast of a patient, the apparatus comprising:
   a single ultrasonic emitter configured to emit a pulse and comprising one or more electro-acoustic transducers;
   a single ultrasonic receiver configured to receive a pulse and comprising one or more electro-acoustic transducers, said emitter and said receiver being in mutually facing relation and at a predetermined distance from each other on opposite sides of a compartment configured for receiving a body under examination, ultrasonic pulses emitted by said emitter and received by said receiver after passing through said body under examination being converted into transmit signals;
   a single combined ultrasonic pulse emitter/receiver comprising one or more electro-acoustic transducers for emitting ultrasonic pulses into said body under examination of a patient and for receiving echoes generated by anatomic structures of said body under examination, said echoes being converted into reflection signals;
   a control unit for controlling said emitter and said emitter/receiver;
   a processing unit for processing signals;
   a unit generating images;
   a unit displaying said images, wherein an acoustic impedance adaptation medium is configured to be interposed between one or more of said emitter, said receiver, or said emitter/receiver, and said body under examination; and
   a shape changing element configured for changing a shape of said body under examination, so that, for most of a surface of said body under examination, lines of view of the ultrasonic pulses emitted by said emitter/receiver are incident on said surface at an angle less than 70° to a normal of a plane tangent to said surface of said body under examination in an incidence point.

2. The apparatus as claimed in claim 1, wherein said body is a breast and said shape changing element is a frusto-conical retaining ring configured to be placed around said breast.

3. The apparatus as claimed in claim 1, wherein said body is a breast and said shape changing element is a retaining cup configured to be placed around said breast.

4. The apparatus as claimed in claim 1, wherein said shape changing element is made of a material having an acoustic wave propagation velocity and a density substantially equal to those of water.

5. The apparatus as claimed in claim 1, wherein said shape changing element is made of a material that is substantially transparent acoustically, such to cause no significant reflection and to adapt to impedance of media between which said shape changing element is interposed, thereby ensuring a lower refraction with a same incidence angle.

6. The apparatus as claimed in claim 5, wherein said material is selected from the group consisting of silicones, polyurethanes, urethanes, and agaroses.

7. The apparatus as claimed in claim 1, wherein a size adjustment element is provided for adjusting a size of said shape changing element.

8. The apparatus as claimed in claim 1, wherein said acoustic impedance medium comprises water added with polyethylene glycol in liquid solution therein.

9. The apparatus as claimed in claim 8, wherein said angle is less than 66°.

10. The apparatus as claimed in claim 8, wherein said polyethylene glycol is added in an amount from 10% to 30% in weight.

11. An apparatus for ultrasound imaging of a body under examination, particularly a breast of a patient, the apparatus comprising:
a single ultrasonic emitter configured to emit a pulse and comprising one or more electro-acoustic transducers;
a single ultrasonic receiver configured to receive a pulse and comprising one or more electro-acoustic transducers, said emitter and said receiver being in mutually facing relation and at a predetermined distance from each other on opposite sides of a compartment configured for receiving a body under examination, ultrasonic pulses emitted by said emitter and received by said receiver after passing through said body under examination being converted into transmit signals;
a single combined ultrasonic pulse emitter/receiver comprising one or more electro-acoustic transducers for emitting ultrasonic pulses into said body under examination of a patient and for receiving echoes generated by anatomical structures of said body under examination, said echoes being converted into reflection signals;
a control unit for controlling said emitter and said emitter/receiver;
a processing unit for processing signals; and
a unit generating images, and a unit displaying said images,
wherein an acoustic impedance adaptation medium is configured to be interposed between one or more of said emitter, said receiver, or said emitter/receiver, and said body under examination; and
wherein said acoustic impedance medium comprises water and polyethylene glycol in liquid solution therein, and wherein said polyethylene glycol is added to the water in an amount from 10% to 30% in weight further comprising
a shape changing element configured for changing the shape of said body under examination, so that, for most of a surface of said body under examination, lines of view of the ultrasonic pulses emitted by said emitter/receiver are incident on said surface at an angle less than 70° to a normal of a plane tangent to said surface of said body under examination in an incidence point,
wherein said emitter/receiver is arranged to define a scan plane substantially perpendicular to the coronal plane of said patient.

12. The apparatus as claimed in claim 11, wherein said body is a breast and said shape changing element is a frusto-conical retaining ring or a retaining cup configured to be placed around said breast.

13. The apparatus as claimed in claim 11, wherein said unit for processing signals generates a propagation velocity map from said transmit signals, said images generated from said reflection signals being further recorded according to said propagation velocity map.

14. The apparatus as claimed in claim 11, wherein said angle is less than 66°.

15. The apparatus as claimed in claim 11, wherein said emitter/receiver is arranged to define a scan plane substantially perpendicular to the coronal plane of said patient.

16. The apparatus as claimed in claim 15, wherein said unit for processing signals generates a propagation velocity map from said transmit signals, said images generated on the basis of said reflection signals being further recorded according to said propagation velocity map.

17. The apparatus as claimed in claim 15, further comprising a second ultrasonic pulse emitter/receiver, said second ultrasonic pulse emitter/receiver comprising one or more electro-acoustic transducers for emitting ultrasonic pulses into said body under examination and receiving echoes generated by the anatomical structures of said body under examination, said echoes being converted into reflection signals, said second emitter/receiver being arranged to define a scan plane substantially parallel to the coronal plane of said patient, images generated by said second emitter/receiver being further combined with said images generated by said emitter/receiver.

18. An apparatus for ultrasound imaging of a body under examination, particularly a breast of a patient, the apparatus comprising:
a single ultrasonic emitter configured to emit a pulse and comprising one or more electro-acoustic transducers;
a single ultrasonic receiver configured to receive a pulse and comprising one or more electro-acoustic transducers, said emitter and said receiver being in mutually facing relation and at a predetermined distance from each other on opposite sides of a compartment configured for receiving a body under examination, ultrasonic pulses emitted by said emitter and received by said receiver after passing through said body under examination being converted into transmit signals;
a single combined ultrasonic pulse emitter/receiver configured to be disposed in substantially perpendicular position to a coronal plane of the patient and comprising one or more electro-acoustic transducers for emitting ultrasonic pulses into said body under examination of a patient and for receiving echoes generated by anatomical structures of said body under examination, said echoes being converted into reflection signals;
a control unit for controlling said emitter and said receiver;
a processing unit for processing signals;
a unit generating images;

a unit displaying said images, wherein an acoustic impedance adaptation medium is configured to be interposed between one or more of said emitter, said receiver, or said emitter/receiver, and said body under examination; and a shape changing element for changing a shape of said body under examination, so that, for most of a surface of said body under examination, lines of view of the ultrasonic pulses emitted by said emitter/receiver are incident on said surface at an angle less than 70° to a normal of a plane tangent to said surface of said body under examination in an incidence point, wherein said emitter/receiver is arranged to define a scan plane substantially perpendicular to said coronal plane of said patient.

19. The apparatus as claimed in claim 18, wherein said body is a breast and said shape changing element is a frusto-conical retaining ring or a retaining cup configured to be placed around said breast.

20. The apparatus as claimed in claim 18, wherein said unit for processing signals generates a propagation velocity map from said transmit signals, said images generated on the basis of said reflection signals being further recorded according to said propagation velocity map.

* * * * *

UNITED STATES PATENT AND TRADEMARK OFFICE
CERTIFICATE OF CORRECTION

| | |
|---|---|
| PATENT NO. | : 8,827,908 B2 |
| APPLICATION NO. | : 13/539061 |
| DATED | : September 9, 2014 |
| INVENTOR(S) | : Paolo Pellegretti, James W. Wiskin and David T. Borup |

It is certified that error appears in the above-identified patent and that said Letters Patent is hereby corrected as shown below:

On the Title Page

Item (75), "Inventor: Paolo Pellegretti, Genova (IT)" should read:
--Inventors: Paolo Pellegretti, Genova (IT); James W. Wiskin, Novato, CA (US); David T. Borup, Salt Lake City, UT (US)--.

Signed and Sealed this
Eighth Day of August, 2023

Katherine Kelly Vidal
*Director of the United States Patent and Trademark Office*